United States Patent

Bartmann et al.

Patent Number: 5,562,858
Date of Patent: Oct. 8, 1996

[54] HEXAFLUOROPROPYL ETHERS, AND LIQUID-CRYSTALLINE MEDIUM

[75] Inventors: Ekkehard Bartmann, Erzhausen; Detlef Pauluth, Ober-Ramstadt; Herbert Plach, Darmstadt, all of Germany

[73] Assignee: Merck Patent Gesellschaft mit beshrankter Haftung, Darmstadt, Germany

[21] Appl. No.: 421,446

[22] Filed: Apr. 13, 1995

[30] Foreign Application Priority Data

Apr. 14, 1994 [DE] Germany ............ 44 12 796.0

[51] Int. Cl.$^6$ ............ C09K 19/12; C09K 19/52; G02F 1/13

[52] U.S. Cl. ............ 252/299.66; 252/299.01; 252/299.61; 252/299.62; 252/299.63; 252/299.64; 252/299.67; 359/103

[58] Field of Search ............ 252/299.01, 299.61, 252/299.62, 299.63, 299.64, 299.65, 299.66, 299.67; 359/103; 570/127, 129, 131

[56] References Cited

U.S. PATENT DOCUMENTS 5,403,512  4/1995  Bartmann et al. ............ 252/299.01

FOREIGN PATENT DOCUMENTS

| 640578 | 3/1995 | European Pat. Off. |
| 4137401 | 5/1993 | Germany. |
| 4215277 | 11/1993 | Germany. |
| 88/00335 | 6/1987 | WIPO. |

*Primary Examiner*—Shean C. Wu
*Attorney, Agent, or Firm*—Millen, White, Zelano, & Branigan, P.C.

[57] ABSTRACT

Hexafluoropropyl ethers of the formula I

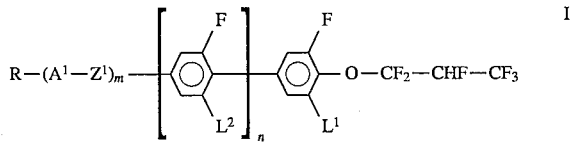

in which R, $A^1$, $Z^1$, $L^1$, $L^2$, m and n are as defined herein are suitable as components of liquid-cyrstalline media.

11 Claims, No Drawings

HEXAFLUOROPROPYL ETHERS, AND LIQUID-CRYSTALLINE MEDIUM

The invention relates to 1,1,2,3,3,3-hexafluoropropyl ethers of the formula I

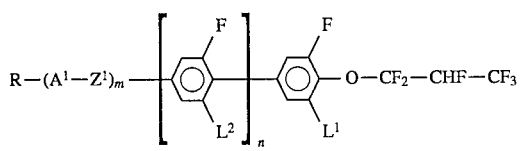

in which

R is H, an alkyl or alkenyl radical having 1 to 15 carbon atoms which is unsubstituted, monosubstituted by CN or CF$_3$ or monosubstituted to perhalo-substituted by halogen, it also being possible for one or more CH$_2$ groups in these radicals to be replaced, in each case independently of one another by —O—, —S—,

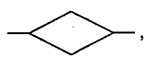

—CO— —CO—O— —O—CO— or —O—CO—O in such a way that O and or S atoms are not linked directly to one another, A$^1$ is
  (a) a trans-1,4-cyclohexylene radical in which, in addition, one or more nonadjacent CH$_2$ groups can, in each case, be replaced by —O— or —S—,
  (b) a 1,4-phenylene radical in which, in addition, one or two CH groups can be replaced by N,
  (c) a radical from the group consisting of 1,4 -cyclohexenylene, 1,4-bicyclo[2.2.2]octylene, piperidine-1,4-diyl, naphthalene-2,6-diyl, decahydronaphthalene-2,6-diyl and 1,2,3,4-tetrahydronaphthalene-2,6-diyl, where the radicals (a) and (b) can be substituted by one or two fluorine atoms, Z$^1$ is —CO—O, —O—CO—, —CH$_2$O—, —OCH$_2$—, —CH$_2$CH$_2$—, —CH=CH—, —C≡C—, —(CH$_2$)$_4$—, —CH=CH—CH$_2$CH$_2$—, or a single bond, m is 0, 1 or 2, n is 0 or 1, where m+n is ≧1, and L$^1$ and L$^2$ are each, independently of one another, H or F.

The invention furthermore relates to the use of these compounds as components of liquid-crystalline media and to liquid-crystal and electro-optical display elements containing the liquid-crystalline media according to the invention.

The compounds of the formula I can be used as components of liquid-crystalline media, in particular for displays based on the principle of the twisted cell, the guest-host effect, the effect of deformation of aligned phases or the effect of dynamic scattering.

The invention has as an object finding novel, stable, liquid-crystalline or mesogenic compounds which are suitable as components of liquid-crystalline media and in particular have at the same time comparatively low viscosity and relatively high dielectric anisotropy.

Upon further study of the specification and appended claims, further objects and advantages of this invention will become apparent to those skilled in the art.

It has now been found that compounds of the formula I are eminently suitable as components of liquid-crystaline media. In particular, they have comparatively low viscosities. They can be used to obtain stable liquid-crystalline media having a broad mesophase range and advantageous values for the optical and dielectric anisotropy. Furthermore, these media have very good low-temperature behavior.

BACKGROUND OF THE INVENTION

In the general formula, WO 88/00335 covers the compounds of the formula I, but the compounds according to the invention are not mentioned therein.

DE-A 42 15 277.1 describes compounds containing a terminal OCH$_2$—CF$_2$—CF$_2$H or —O—CH$_2$—CF$_2$—CF$_3$ end group, such as, for example,

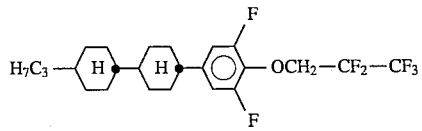

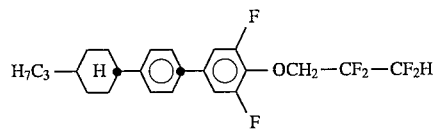

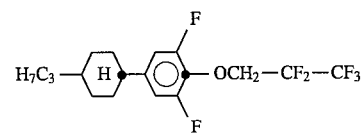

However, in view of the very wide range of areas of application of such compounds having high Δε, dielectric anisotropy, it was desirable to have available further compounds of high nematogeneity, i.e., with good nematic properties, which have properties precisely customized to the particular applications.

DESCRIPTION OF PREFERRED EMBODIMENTS OF THE INVENTION

In addition, the provision of compounds of the formula I very generally considerably broadens the range of liquid-crystalline substances which are suitable, from various applicational points of view, for the preparation of liquid-crystalline mixtures.

The compounds of the formula I have a broad range of applications. Depending on the choice of substituents, these compounds can be used as base materials from which liquid-crystalline media are predominantly composed; however, it is also possible to add compounds of the formula I to liquid-crystalline base materials from other classes of compound in order, for example, to modify the dielectric and/or optical anisotropy of a dielectric of this type and/or to optimize its threshold voltage and/or its viscosity.

In the pure state, the compounds of the formula I are colorless and form liquid-crystalline mesophases in a temperature range which is favorably located for electro-optical use. They are stable chemically, thermally and to light.

The invention thus relates to the compounds of the formula I and to the use of these compounds as components of liquid-crystalline media. The invention furthermore relates to liquid-crystalline media containing at least one compound of the formula I and to liquid-crystal display elements, in particular electro-optical display elements, containing media of this type.

For reasons of simplicity, $A^3$ and $A^2$ below are a radical of the formula

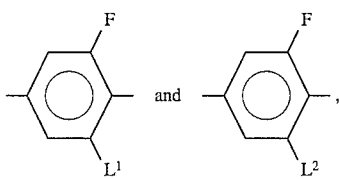

respectively, Y is $OCF_2$—CHF—$CF_3$, Cyc denotes a 1,4-cyclohexyl radical, Che denotes a 1,4-cyclohexenylene radical, Dio denotes a 1,3-dioxane-2,5-diyl radical, Dit denotes a 1,3-dithiane-2,5-diyl radical, Phe denotes a 1,4-phenylene radical, Pyd denotes a pyridine-2,5-diyl radical, Pyr denotes a pyrimidine-2,5-diyl radical and Bi denotes a bicyclo[2.2.2]octylene radical, where Cyc and/or Phe can be unsubstituted or monosubstituted or disubstituted by F.

$A^1$ is preferably selected from the group consisting of Cyc, Che, Phe, Pyr, Pyd and Dio.

Accordingly, the compounds of the formula I cover bicyclic compounds of the subformulae Ia to Ic:

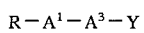 Ia

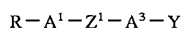 Ib

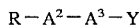 Ic tricyclic compounds of the fubformulae Id to Ig:

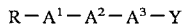 Id

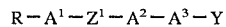 Ie

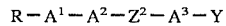 If

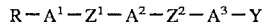 Ig and tetracyclic compounds of the subformulae Ih to Ik:

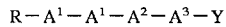 Ih

 Ii

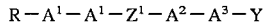 Ij

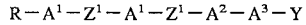 Ik

Of these, particular preference is given to the compounds of the subformulae Ia, Id, Ie, If and Ih.

The preferred compounds of the subformula Ia include those of the subformulae Iaa to Iaf:

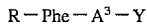 Iaa

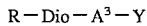 Iab

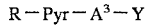 Iac

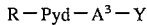 Iad

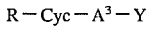 Iae

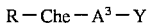 Iaf

Of these, those of the formulae Iaa and Iae are particularly preferred.

Preference is also given to compounds of the formula I and all of the subformulae in which $A^1$, $A^2$ and/or $A^3$ is 1,4-phenylene which is monosubstituted or disubstituted by F, in particular, 2-fluoro-1,4-phenylene, 3-fluoro-1,4-phenylene or 3,5-difluoro-1,4-phenylene.

$A^1$ is preferably

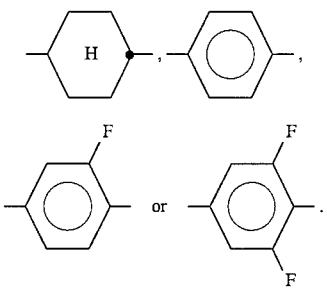

$Z^1$ is preferably a single bond, —CO—O—, —O—CO— or —$CH_2CH_2$—, secondarily preferably —$CH_2O$— or —$OCH_2$—.

m is preferably 1 or 0, particularly preferably 1.

If R is an alkyl radical or an alkoxy radical, i.e., where the first —$CH_2$— group is replaced by —O—, it may be straight-chain or branched, and, when branched, may be optically active. It is preferably straight chain, has 2, 3, 4, 5, 6 or 7 carbon atoms and accordingly is preferably ethyl, propyl, butyl, pentyl, hexyl, heptyl, ethoxy, propoxy, butoxy, pentoxy, hexoxy or heptoxy, furthermore methyl, octyl, nonyl, decyl, undecyl, dodecyl, tridecyl, tetradecyl, pentadecyl, methoxy, octoxy, nonoxy, decoxy, undecoxy, dodecoxy, tridecoxy or tetradecoxy.

When R is oxaalkyl, it is preferably straight chain 2-oxapropyl (=methoxymethyl), 2-(=ethoxymethyl) or 3-oxabutyl (=2-methoxyethyl), 2-, 3- or 4-oxapentyl, 2-, 3-, 4- or 5-oxahexyl, 2-, 3-, 4-, 5- or 6-oxaheptyl, 2-, 3-, 4-, 5-, 6- or 7-oxaoctyl, 2-, 3-, 4-, 5-, 6-, 7- or 8-oxanonyl, or 2-, 3-, 4-, 5-, 6-, 7-, 8- or 9-oxadecyl.

If R is an alkenyl radical, i.e., where there is a —CH=CH— group in the chain, it may be straight-chain or branched. It is preferably straight-chain and has 2 to 10 carbon atoms. Accordingly it is in particular vinyl, prop-1- or -2-enyl, but-1-, -2- or -3-enyl, pent-1-, -2-, -3- or -4-enyl, hex-1-, -2-, -3-, -4- or -5-enyl, hept-1-, -2-, -3-, -4-, -5- or -6-enyl, oct-1-, -2-, -3-, -4-, -5-, -6- or -7-enyl, non-1-, -2-, -3-, -4-, -5-, -6-, -7- or -8-enyl, or dec-1-, -2-, -3-, -4-, -5-, -6-, -7-, -8- or-9-enyl.

If R is an alkyl radical in which one $CH_2$ group has been replaced by —O— and one has been replaced by —CO—, these are preferably adjacent. Thus, such R groups preferably contain one acyloxy group —CO—O— or one oxycarbonyl group —O—CO—. This is preferably straight-chain and has 2 to 6 carbon atoms. In this case, R is particularly preferably acetoxy, propionyloxy, butyryloxy, pentanoyloxy, hexanoyloxy, acetoxymethyl, propionyloxymethyl, butyryloxymethyl, pentanoyloxymethyl, 2-acetoxyethyl, 2-propionyloxyethyl, 2-butyryloxyethyl, 3-acetoxy-propyl, 3-propionyloxypropyl, 4-acetoxybutyl, methoxycarbonyl, ethoxycarbonyl, propoxycarbonyl, butoxycarbonyl, pentaoxycarbonyl, methoxycarbonylmethyl, ethoxycarbonylmethyl, propoxycarbonylmethyl, butoxycarbonylmethyl, 2-(methoxycarbonyl)ethyl, 2-(ethoxycarbonyl)ethyl, 2-(propoxycarbonyl)ethyl, 3-(methoxycarbonyl)propyl, 3-(ethoxycarbonyl)propyl or 4-(methoxycarbonyl)butyl.

If R is an alkenyl radical, i.e., having an unsubstituted or substituted —CH=CH— group, and a $CH_2$ group adjacent a carbon which is double bonded has been replaced by CO or CO—O or —O—CO—, this may be straight-chain or branched. It is preferably straight-chain and has 4 to 13 carbon atoms. Accordingly it is in particular acryloyloxymethyl, 2-acryloyloxyethyl, 3-acryloyloxypropyl, 4-acryloyloxybutyl, 5-acryloyloxypentyl, 6-acryloyloxyhexyl, 7-acryloyloxyheptyl, 8-acryloyloxyoctyl, 9-acryloyloxynonyl, 10-acryloyloxydecyl, methacryloyloxymethyl, 2-methacryloyloxyethyl, 3-methacryloyloxypropyl, 4-methacryloyloxybutyl, 5-methacryloyloxypentyl, 6-methacryloyloxyhexyl, 7-methacryloyloxyheptyl, 8-methacryloyloxyoctyl or 9-methacryloyloxynonyl.

If R is an alkyl or alkenyl radical which is monosubstituted by CN or $CF_3$, this radical is preferably straight-chain and the substitution by CN or $CF_3$ is in the ω-position.

If R is an alkyl or alkenyl radical which is monosubstituted to perhalo-substituted by halogen, this radical is preferably straight-chain and halogen is preferably F or Cl. In the case of multiple substitution, halogen is preferably F. The resulting radicals thus include perfluorinated radicals. In the case of monosubstitution, the fluorine or chlorine substituent can be in any desired position, but is preferably in the ω-position.

Compounds of the formula I which contain wing groups R which are suitable for polymerization reactions are suitable for the preparation of liquid-crystalline polymers.

Compounds of the formula I containing branched wing groups R may occasionally be of importance due to better solubility in the customary liquid-crystalline base materials, but in particular as chiral dopes if they are optically active. Smectic compounds of this type are suitable as components of ferroelectric materials.

Compounds of the formula I having $S_A$ phases are suitable, for example, for thermally addressed displays.

Branched groups of this type preferably contain not more than one chain branch. Preferred branched radicals R are isopropyl, 2-butyl (=1-methylpropyl), isobutyl (=2-methylpropyl), 2-methylbutyl, isopentyl (=3-methylbutyl), 2-methylpentyl, 3-methylpentyl, 2 ethylhexyl, 2-propylpentyl, isopropoxy, 2-methylpropoxy, 2-methylbutoxy, 3-methylbutoxy, 2-methylpentoxy, 3-methylpentoxy, 2-ethylhexoxy, 1-methylhexoxy and 1-methylheptoxy.

If R is an alkyl radical in which two or more $CH_2$ groups have been replaced by —O— and/or —CO—O—, this may be straight-chain or branched. It is preferably branched and has 3 to 12 carbon atoms. Accordingly it is in particular biscarboxymethyl, 2,2-biscarboxyethyl, 3,3-biscarboxypropyl, 4,4-biscarboxybutyl, 5,5-biscarboxypentyl, 6,6-biscarboxyhexyl, 7,7-biscarboxyheptyl, 8,8-biscarboxyoctyl, 9,9-biscarboxynonyl, 10,10-biscarboxydecyl, bis(methoxycarbonyl)methyl, 2,2-bis(methoxycarbonyl)ethyl, 3,3-bis(methoxycarbonyl)propyl, 4,4-bis(methoxycarbonyl)butyl, 5,5-bis(methoxycarbonyl)pentyl, 6,6-bis(methoxycarbonyl)hexyl, 7,7-bis(methoxycarbonyl)heptyl, 8,8-bis(methoxycarbonyl)octyl, bis(ethoxycarbonyl)methyl, 2,2-bis(ethoxycarbonyl)ethyl, 3,3-bis(ethoxycarbonyl)propyl, 4,4-bis(ethoxycarbonyl)butyl or 5,5-bis(ethoxycarbonyl)hexyl.

Compounds of the formula I which contain wing groups R which are suitable for polycondensations are suitable for the preparation of liquid-crystalline polycondensates.

The formula I covers the racemates of these compounds and the optical antipodes, and mixtures thereof.

Of these compounds of the formula I and of the subformulae, preference is given to those in which at least one of the radicals present therein has one of the preferred meanings mentioned.

In the compounds of the formula I, preference is also given to stereoisomers in which the rings Cyc and Piperidine are trans-1,4-disubstituted. Those of the abovementioned formulae which contain one or more groups Pyd, Pyr and/or Dio in each case include the two 2,5-positional isomers.

Preferred subgeneric groups of compounds are those of the subformulae I1 to I32:

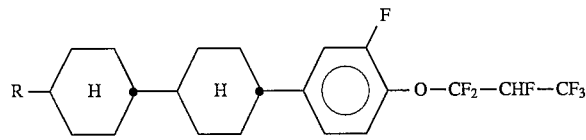

I1

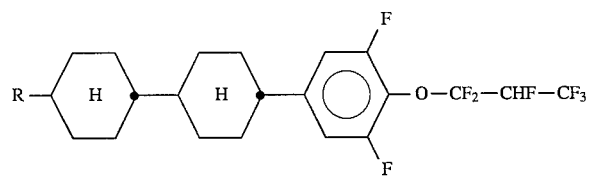

I2

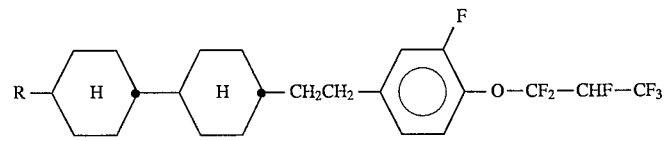

I3

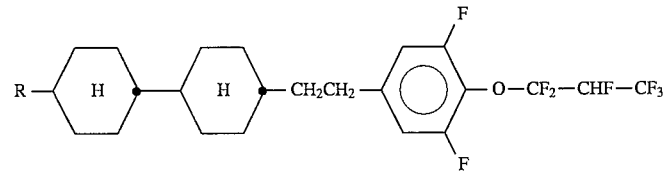

I4

-continued
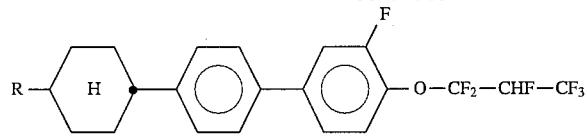 I5
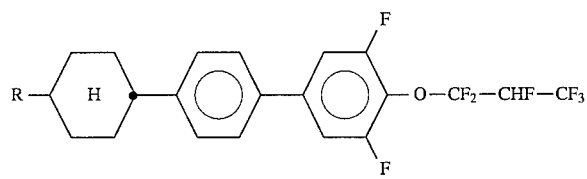 I6
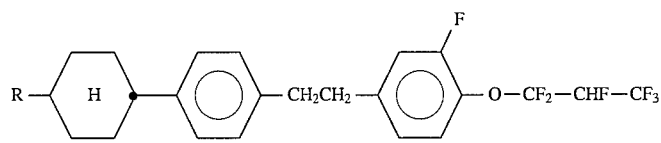 I7
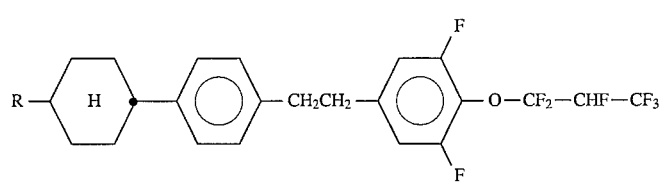 I8
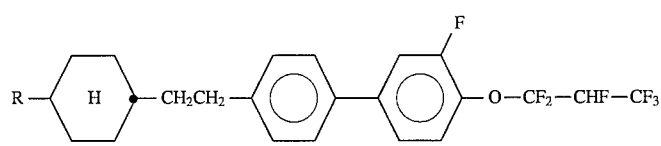 I9
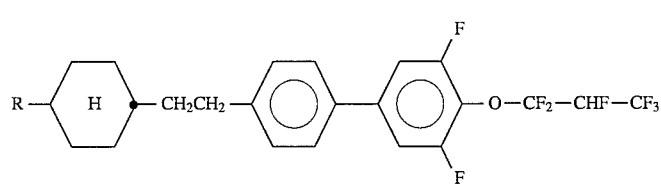 I10
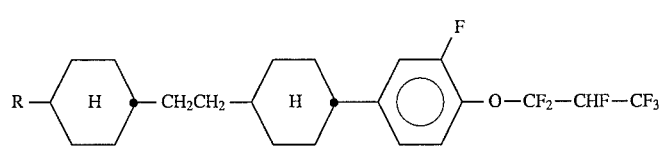 I11
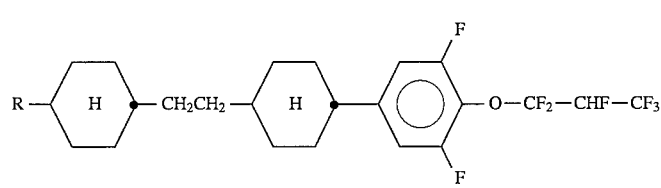 I12
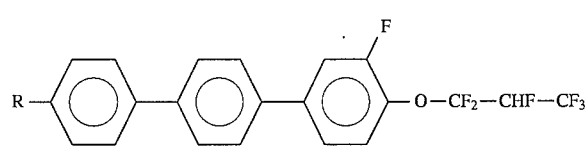 I13
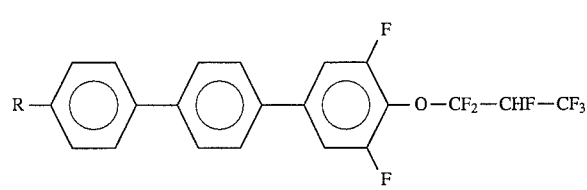 I14

-continued
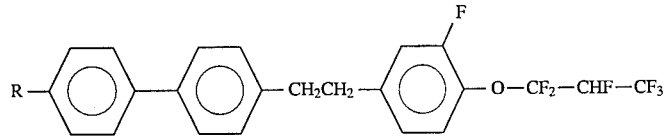 I15
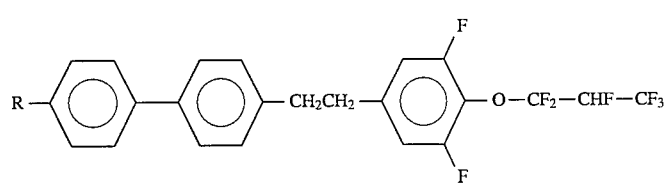 I16
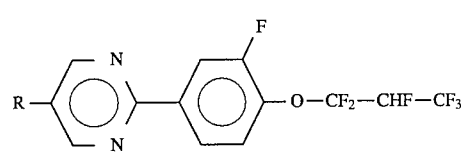 I17
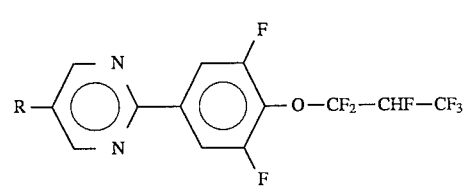 I18
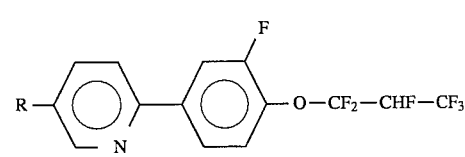 I19
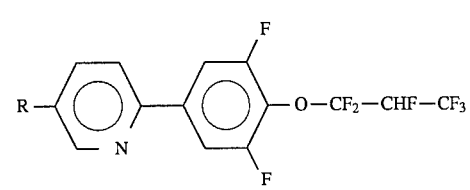 I20
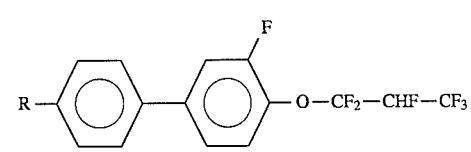 I21
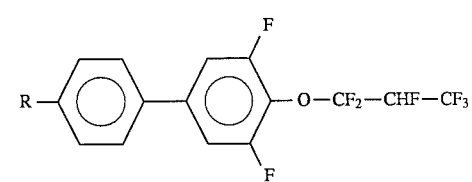 I22
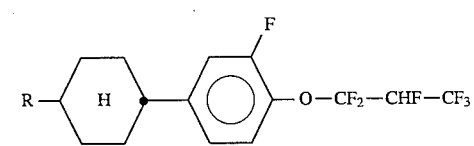 I23
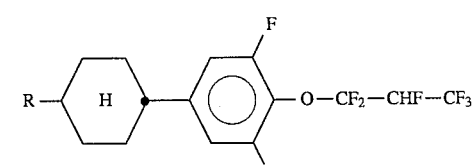 I24

-continued

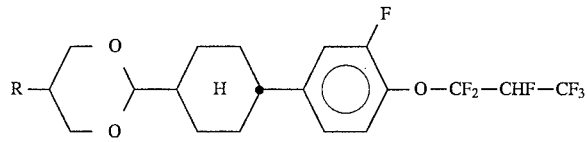
I25

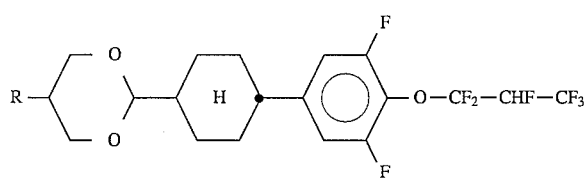
I26

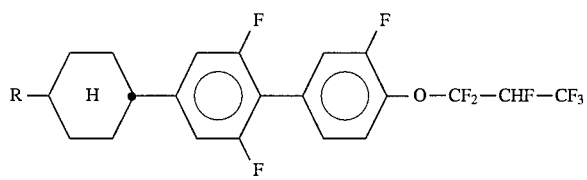
I27

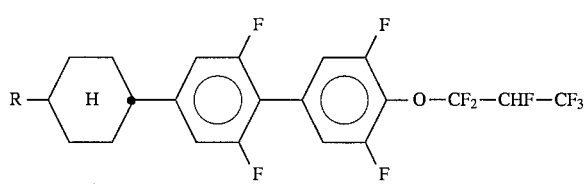
I28

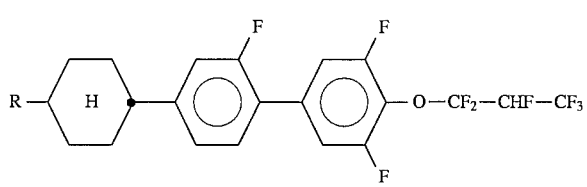
I29

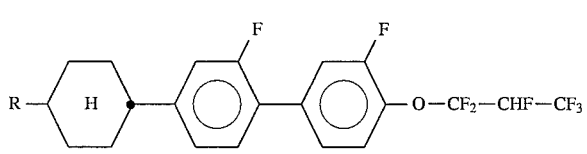
I30

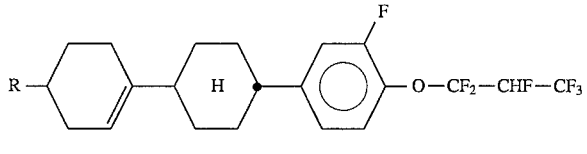
I31

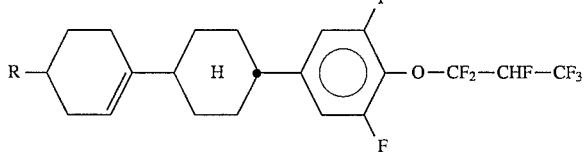
I32

The 1,4-cyclohexenylene group preferably has the following structures:

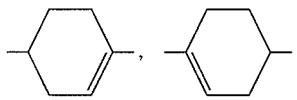

The compounds of the formula I are preparable by methods known per se, as described in the literature (for example in the standard works such as Houben-Weyl, Methoden der Organischen Chemie, Georg-Thieme-Verlag, Stuttgart), to be precise under reaction conditions which are known and suitable for said reactions.

Use may also be made of variants which are known per se, but are not mentioned here in greater detail.

The novel compounds can be prepared, for example, by metalating a compound of the formula II

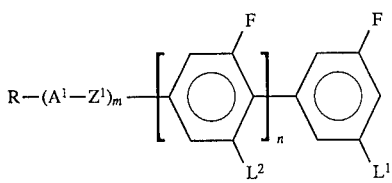   II in which R, $A^1$, $A^2$, $Z^1$, $Z^2$, m and n are as defined above, and $L^1$ and $L^2$ are H or F, as shown in the reaction scheme below, and subsequently reacting the product with a suitable electrophile:

Scheme 1

($L^1$ and $L^2$ = H or F)

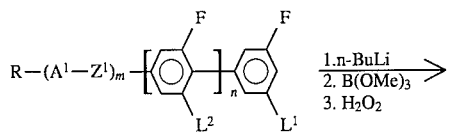

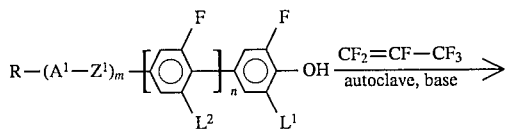

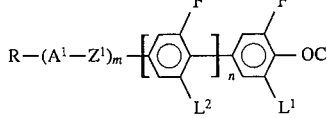

The target products are obtainable from the resultant phenol by known methods, for example by reacting the phenol with hexafluoro-1-propene.

Other synthetic methods are apparent to the person skilled in the art. For example, appropriately 5-substituted 1,3-difluorobenzene compounds or monofluorinated analogs ($L^2$=H) can be converted into the 1,3-difluoro compounds or monofluorinated analogs ($L^2$=H) in accordance with the above scheme, and the radical R—$(A^1$—$Z^1)_m$—$A^2$—$Z^2$ can subsequently be introduced by reactions which are customary in liquid-crystal chemistry (for example esterification, etherification or coupling, for example as described in the article by E. Poetsch, Kontakte (Darmstadt) 1988 (2), p. 15).

The compounds of the formula II can be prepared, for example, by the synthetic schemes below:

Scheme 2

[A = —$(A^1$—$Z^1)_{m-1}$—$A^1$—]

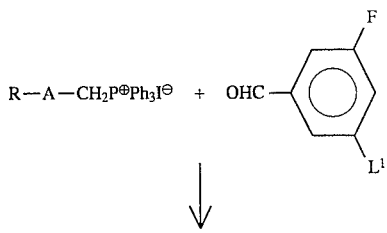

-continued
Scheme 2

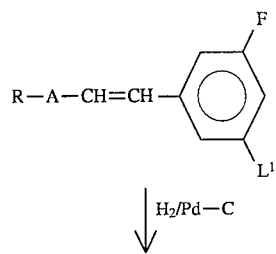

Scheme 3

[A = —$(A^1$—$Z^1)_{m-1}$—$A^1$]

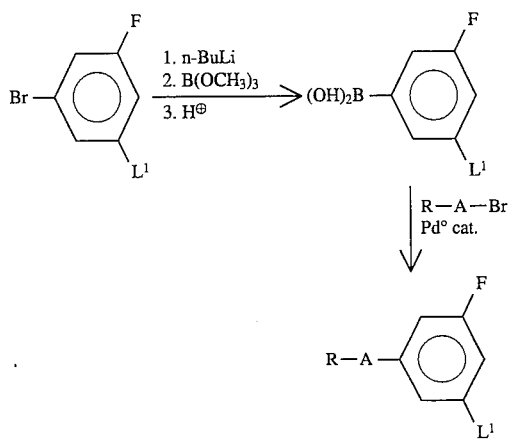

Scheme 4

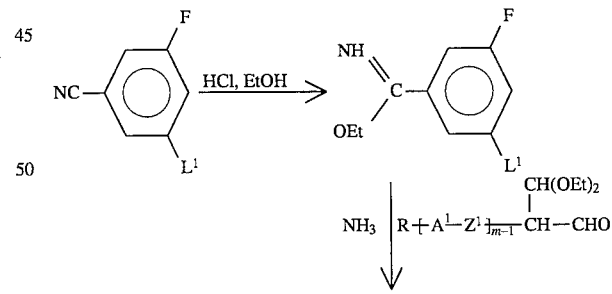

Scheme 4 -continued

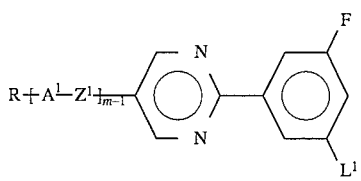

Scheme 5

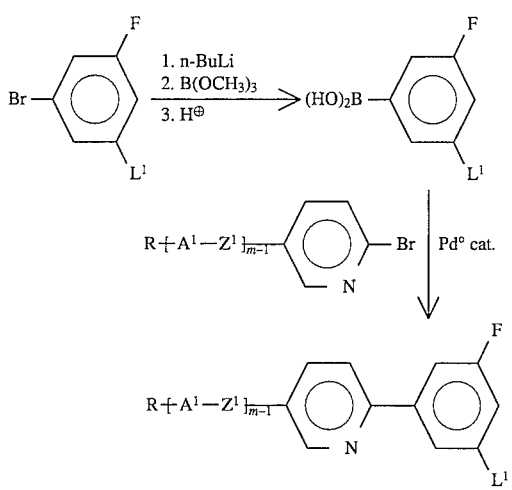

Scheme 6

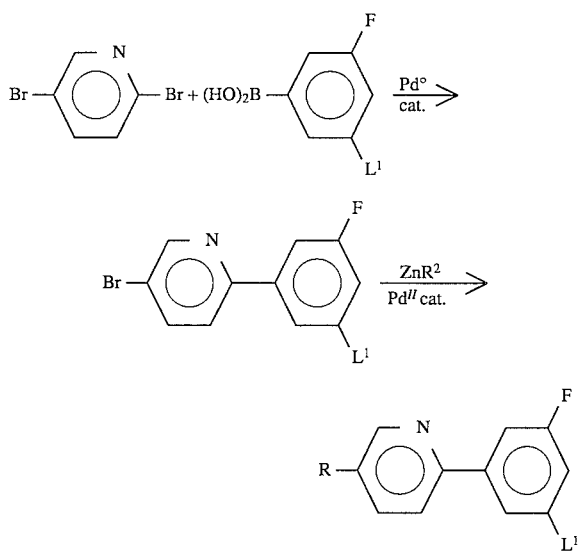

The starting materials are either known or can be prepared analogously to known compounds.

Esters of the formula I can also be obtained by esterification of corresponding carboxylic acids (or reactive derivatives thereof) using alcohols or phenols (or reactive derivatives thereof) or by the DCC method (DCC= dicyclohexylcarbodiimide).

The corresponding carboxylic acids and alcohols or phenols are known or can be prepared analogously to known processes.

In a further process for the preparation of the compounds of the formula I, an aryl halide is reacted with an olefin in the presence of a tertiary amine and in the presence of a palladium catalyst (cf. R. F. Heck, Acc. Chem. Res. 12(1979) 146). Examples of suitable aryl halides are chlorides, bromides and iodides, in particular bromides and iodides. The tertiary amines which are necessary for the success of the coupling reaction, such as, for example, triethylamine, are also suitable as solvent. Examples of suitable palladium catalysts are palladium salts, in particular Pd(II) acetate, with organophosphorus(III) compounds, such as, for example, triarylphosphines. The reaction can be carried out in the presence or absence of an inert solvent at temperatures of about 0° to 150° C., preferably of 20°0 to 100° C.; suitable solvents are, for example, nitriles, such as acetonitrile, or hydrocarbons, such as benzene or toluene. The aryl halides and olefins employed as starting materials are frequently commercially available or can be prepared by processes known from the literature, for example by halogenation of corresponding parent compounds or by elimination reactions on corresponding alcohols or halides.

Stilbene derivatives, for example, can be prepared in this way. The stilbenes can also be prepared by reacting a 4-substituted benzaldehyde with a corresponding phosphorus ylide by the Wittig method. However, tolans of the formula I can also be prepared by employing monosubstituted acetylene instead of the olefin (Synthesis 627 (1980) or Tetrahedron Lett. 27, 1171 (1986)).

Aromatic compounds can also be coupled by reacting aryl halides with aryltin compounds. These reactions are preferably carried out with addition of a catalyst, such as, for example, a palladium(O)complex, in inert solvents, such as hydrocarbons, at high temperatures, for example in boiling xylene under a protective gas.

Coupling reactions of alkynyl compounds with aryl halides can be carried out analogously to the process described by A. O. King, E. Negishi, F. J. Villani and A. Silveira in J. Org. Chem. 43, 358 (1978).

Tolans of the formula I can also be prepared by Fritsch-Buttenberg-Wiechell rearrangement (Ann. 279, 319, 1984), in which 1,1-diaryl-2-haloethylenes are rearranged in the presence of strong bases to give diarylacetylenes.

Tolans of the formula I can also be prepared by brominating the corresponding stilbenes and then dehydrohalogenating the product. Use can also be made here of variants of this reaction which are not mentioned in greater detail.

Ethers of the formula I are obtainable by etherification of corresponding hydroxyl compounds, preferably corresponding phenols, the hydroxyl compound expediently first being converted into a corresponding metal derivative, for example into the corresponding alkali metal alkoxide or alkali metal phenoxide by treatment with NaH, NaNH$_2$, NaOH, KOH, Na$_2$CO$_3$ or K$_2$CO$_3$. This metal derivative can then be reacted with the appropriate alkyl halide, alkyl sulphonate or dialkyl sulphonate, expediently in an inert solvent, such as, for example, acetone, 1,2-dimethoxyethane, DMF or dimethyl sulphoxide or alternatively with an excess of aqueous or aqueous-alcoholic NaOH or KOH at temperatures of about 20° to 100° C.

The starting materials are either known or can be prepared analogously to known compounds.

The preferred trans-isomers can be prepared by the isomerization methods known from the literature. Any intermediates obtained in which R$^o$=H are converted into the compounds of the formula I' entirely analogously to the precursors of the compounds of the formula I by introduction of the radical -Y.

The aldehydes can be obtained by Heck reaction of appropriately substituted 1-bromo-3-fluorobenzene derivatives with allyl alcohol.

The synthesis of some particularly preferred compounds is shown in greater detail below.

Scheme 7

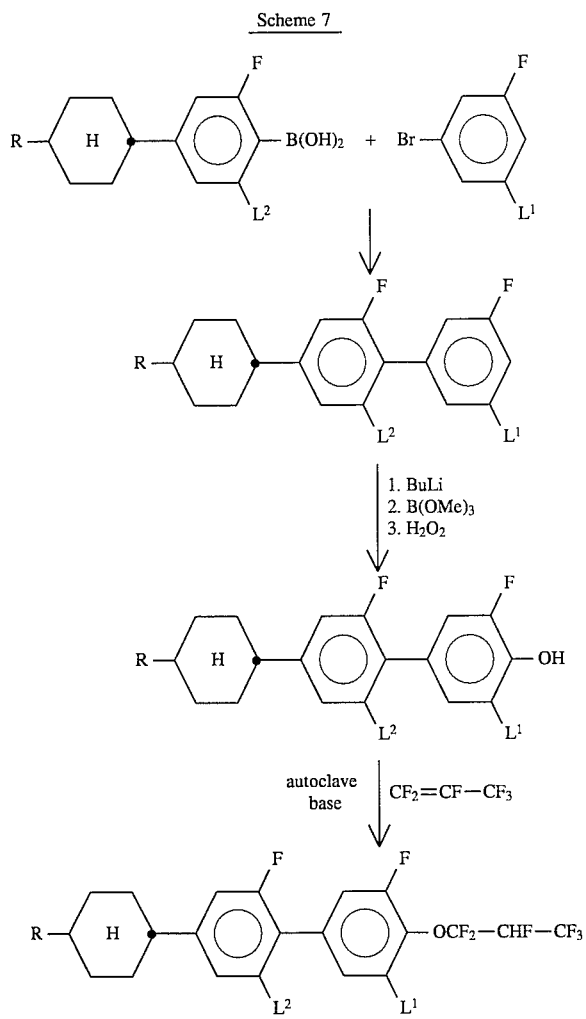

Scheme 8

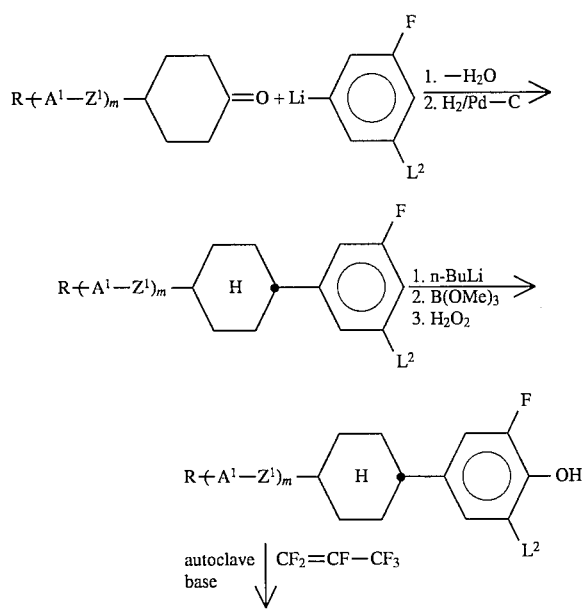

-continued
Scheme 8

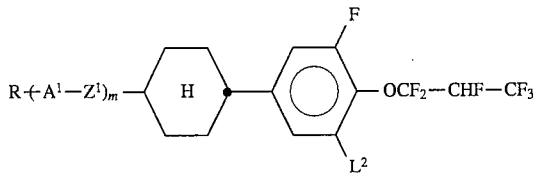

The liquid-crystalline media according to the invention preferably contain 2 to 40, in particular 4 to 30, components as further constituents besides one or more compounds according to the invention. These media very particularly preferably contain 7 to 25 components besides one or more compounds according to the invention. These further constituents are preferably selected from nematic or nematogenic (monotropic or isotropic) substances, in particular substances from the classes of the azoxybenzenes, benzylideneanilines, biphenyls, terphenyls, phenyl or cyclohexyl benzoates, phenyl or cyclohexyl esters of cyclohexanecarboxylic acid, phenyl or cyclohexyl esters of cyclohexylbenzoic acid, phenyl or cyclohexyl esters of cyclohexylcyclohexanecarboxylic acid, cyclohexylphenyl esters of benzoic acid, of cyclohexanecarboxylic acid and of cyclohexylcyclohexanecarboxylic acid, phenylcyclohexanes, cyclohexylbiphenyls, phenylcyclohexylcyclohexanes, cyclohexylcyclohexanes, cyclohexylcyclohexenes, 1,4-bis-cyclohexylbenzenes, 4,4'-bis-cyclohexylbiphenyls, phenyl- or cyclohexylpyrimidines, phenyl- or cyclo-hexylpyridines, phenyl- or cyclohexyldioxanes, phenyl- or cyclohexyl-1,3-dithianes, 1,2-diphenylethanes, 1,2-dicyclohexylethanes, 1-phenyl-2-cyclohexylethanes, 1-cyclohexyl-2-(4-phenylcyclohexyl)ethanes, 1-cyclohexyl-2-biphenylylethanes, 1-phenyl-2-cyclohexylphenylethanes, optionally halogenated stilbenes, benzyl phenyl ethers, tolans and substituted cinnamic acids. The 1,4-phenylene groups in these compounds may also be fluorinated.

The most important compounds suitable as further constituents of media according to the invention can be characterized by the formulae 1, 2, 3, 4 and 5:

| | |
|---|---|
| R'—L—E—R" | 1 |
| R'—L—COO—E—R" | 2 |
| R'—L—OOC—E—R" | 3 |
| R'—L—CH$_2$CH$_2$—E—R" | 4 |
| R'—L—C≡C—E—R" | 5 |

In the formulae 1, 2, 3, 4 and 5, L and E, which may be identical or different, are in each case, independently of one another, a bivalent radical from the group formed by —Phe—, —Cyc—, —Phe—Phe—, —Phe—Cyc—, —Cyc—Cyc—, —Pyr—, —Dio—, —G—Phe— and —G—Cyc— and their mirror images, where Phe is unsubstituted or fluorine-substituted 1,4-phenylene, Cyc is trans-1,4-cyclohexylene or 1,4-cyclohexenylene, Pyr is pyrimidine-2,5-diyl or pyridine-2,5-diyl, Dio is 1,3-dioxane-2,5-diyl and G is 2-(trans-1,4-cyclohexyl)ethyl, pyrimidine-2,5-diyl, pyridine-2,5-diyl or 1,3-dioxane-2,5-diyl.

One of the radicals L and E is preferably Cyc, Phe or Pyr. E is preferably Cyc, Phe or Phe—Cyc. The media according to the invention preferably contain one Or more components selected from the compounds of the formulae 1, 2, 3, 4 and 5 in which L and E are selected from the group consisting of Cyc, Phe and Pyr and simultaneously one or more components selected from the compounds of the formulae 1, 2, 3, 4 and 5 in which one of the radicals L and E is selected from the group consisting of Cyc, Phe and Pyr and the other radical is selected from the group consisting of —Phe—Phe—, —Phe—Cyc—, —Cyc—Cyc—, —G—Phe— and —G—Cyc—, and optionally one or more components selected from the compounds of the formulae 1, 2, 3, 4 and 5 in which the radicals L and E are selected from the group consisting of —Phe—Cyc—, —Cyc—Cyc—, —G—Phe— and —G—Cyc—.

In a smaller sub-group of the compounds of the formulae 1, 2, 3, 4 and 5, R' and R" are in each case, independently of one another, alkyl, alkenyl, alkoxy, alkoxyalkyl, alkenyloxy or alkanoyloxy having up to 8 carbon atoms. This smaller sub-group is called group A below, and the compounds are labelled with the subformulae 1a, 2a, 3a, 4a and 5a. In most of these compounds, R' and R" are different from one another, one of these radicals usually being alkyl, alkenyl, alkoxy or alkoxyalkyl.

In another smaller sub-group of the compounds of the formulae 1, 2, 3, 4 and 5 which is known as group B, R" is —F, —Cl, —NCS or —(O)$_i$CH$_{3-(k+1)}$F$_k$Cl$_1$, where i is 0 or 1, and k+1 is 1, 2 or 3; the compounds in which R" has this meaning are labelled with the subformulae 1b, 2b, 3b, 4b and 5b. Particular preference is given to those compounds of the sub-formulae 1b, 2b, 3b, 4b and 5b in which R" is —F, —Cl, —NCS, —CF$_3$, —OCHF$_2$ or —OCF$_3$.

In the compounds of the sub-formulae 1b, 2b, 3b, 4b and 5b, R' is as defined for the compounds of the sub-formulae 1a–5a and is preferably alkyl, alkenyl, alkoxy or alkoxyalkyl.

In a further smaller sub-group of the compounds of the formulae 1, 2, 3, 4 and 5, R" is —CN; this subgroup is known as group C below, and the compounds of this sub-group are correspondingly described by subformulae 1c, 2c, 3c, 4c and 5c. In the compounds of the sub-formulae 1c, 2c, 3c, 4c and 5c, R' is as defined for the compounds of the sub-formulae 1a–5a and is preferably alkyl, alkoxy or alkenyl.

In addition to the preferred compounds of groups A, B and C, other compounds of the formulae 1, 2, 3, 4 and 5 having other variants of the proposed substituents are also customary. All these substances can be obtained by methods which are known from the literature or analogously thereto.

Besides compounds of the formula I according to the invention, the media according to the invention preferably contain one or more compounds selected from group A and/or group B and/or group C. The proportions by weight of the compounds from these groups in the media according to the invention are preferably Group A: 0 to 90%, preferably 20 to 90%, in particular 30 to 90%

Group B: 0 to 80%, preferably 10 to 80%, in particular 10 to 65%

Group C: 0 to 80%, preferably 5 to 80%, in particular 5 to 50%, the sum of the proportions by weight of the group A and/or B and/or C compounds present in the particular media according to the invention preferably being 5 to 90% and in particular 10 to 90%.

The media according to the invention preferably contain 1 to 40%, particularly preferably 5 to 30%, of compounds according to the invention. Further preferred media are those which contain more than 40%, in particular 45 to 90%, of compounds according to the invention. The media preferably contain three, four or five compounds according to the invention.

The media according to the invention are prepared in a manner which is customary per se. In general, the components are dissolved in one another, expediently at elevated temperature. By means of suitable additives, the liquid-crystalline phases can be modified in accordance with the invention in a manner such that they can be used in all types of liquid-crystal display elements which have hitherto been disclosed. Additives of this type are known to those skilled in the art and are described in detail in the literature (H. Kelker/R. Hatz, Handbook of Liquid Crystals, Verlag Chemie, Weinheim, 1980). For example, pleochroic dyes can be added for the production of colored guest-host systems, or substances can be added to modify the dielectric anisotropy, the viscosity and/or the alignment of the nematic phases.

The examples below are intended to illustrate the invention without representing a limitation. Above and below, percentages are in percent by weight. All temperatures are given in degrees Celsius. m.p. denotes melting point, c.p.= clearing point. Furthermore, C=crystalline state, N=nematic phase, S=smectic phase and I=isotropic phase. The numbers between these symbols represent the transition temperatures. βn denotes optical anisotropy (589 nm, 20° C.), and the viscosity (mm$^2$/sec) was determined at 20° C.

"Customary work-up" means that water is added if appropriate, the mixture is extracted, for example, with dichloromethane, diethyl ether or toluene, the phases are separated, the organic phase is dried and evaporated, and the product is purified by distillation under reduced pressure or crystallization and/or chromatography. The following abbreviations are used:

DAST diethylaminosulphur trifluoride
DMEU 1,3-dimethyl-2-imidazolidinone
POT potassium tertiary-butanolate
THF tetrahydrofuran
pTSOH p-toluenesulphonic acid

PREPARATION EXAMPLE

Example 1

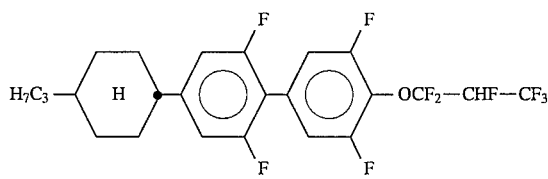

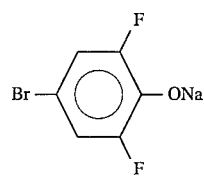

Step 1.1

1.0 mol of sodium hydride are suspended in 200 ml of THF at 0° C. under a nitrogen atmosphere. 1.0 ml of 4-bromo-2,6-difluorophenol, dissolved in 400 ml of THF, is added dropwise to the suspension. The mixture is allowed to warm to room temperature, and is stirred for a further 0.5 hour, filtered and evaporated on a Rotavapor. The residue is dissolved in 150 ml of toluene and re-evaporated until crystals form. The product is recrystallized in petroleum ether.

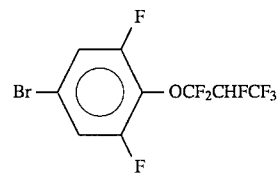

Step 1.2

0.2 mol of 4-bromo-2,6-difluorophenol and 0.02 mol of sodium 4-bromo-2,6-difluorophenoxide are dissolved in 400 ml of DMEU. 0.66 mol of hexafluoropropene are introduced into the solution at 5° C. The solution is subsequently heated at 120° C. for 16 hours in an autoclave. The mixture is allowed to cool to room temperature and is poured into water. The organic phase is separated off and subjected to customary work-up.

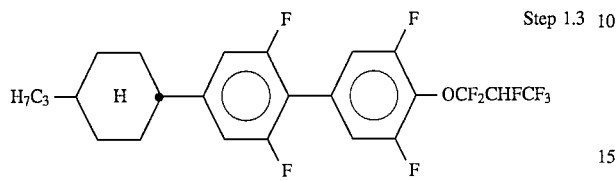

Step 1.3

A solution of 0.02 mol of 4-bromo-2,6-difluoro-1,1,2,3,3,3-hexafluoropropyl ether in 85 ml of THF is heated to 60° C., and 0.02 mol of p-trans-[4-propylcyclohexyl]-2,6-difluorophenylboronic acid and a solution of 0.02 mol of potassium dihydrogenphosphate and 0.04 mol of sodium hydrogenphosphate and 40 ml of water are added. 0.33 g of tetrakis(triphenylphosphine)palladium(O) is added, and the mixture is stirred overnight at 70° C. The mixture is subsequently allowed to cool to room temperature. The organic phase is separated off and subjected to customary work-up. The following properties are observed. C 68 N 91.5 I; $\Delta n=0.107$; $\Delta \epsilon=13.8$.

The following compounds of the formula

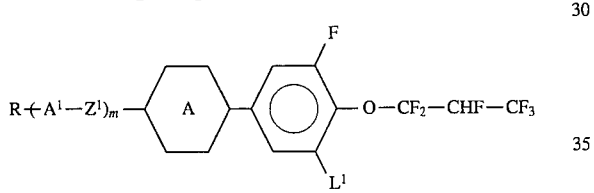

are prepared analogously:

| R | $-(A^1-Z^1)_m-\boxed{A}-$ | $L^1$ | |
|---|---|---|---|
| CH$_3$ | 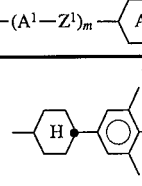 | H | |
| CH$_3$ | 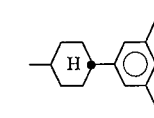 | F | |
| C$_2$H$_5$ | 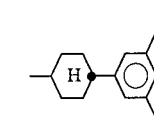 | H | |
| C$_2$H$_5$ | 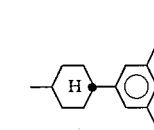 | F | |
| n-C$_3$H$_7$ | 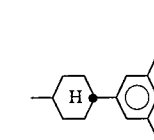 | H | |
| n-C$_4$H$_9$ | 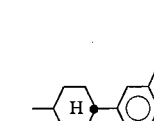 | H | |
| n-C$_4$H$_9$ |  | F | |
| n-C$_5$H$_{11}$ |  | H | |
| n-C$_5$H$_{11}$ | 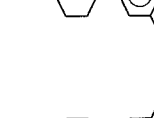 | F | F C 76 N 96.2 I $\Delta n = +0.111$; $\Delta \epsilon = 13.5$ |
| n-C$_6$H$_{13}$ | 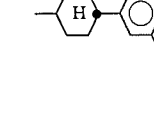 | H | |
| n-C$_6$H$_{13}$ | 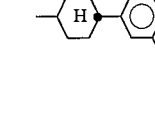 | F | |
| H$_2$C=CH— | 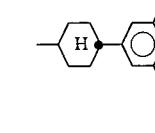 | H | |
| H$_2$C=CH— | | F | |
| H$_3$C—CH=CH— | | H | |
| H$_3$C—CH=CH— | | F | |

-continued

| R | $-(A^1-Z^1)_m-\underset{A}{\bigcirc}-L^1$ | | |
|---|---|---|---|
| C$_2$H$_5$ | [Cy-Phe] | F | H |
| C$_2$H$_5$ | [Cy-Phe] | F | F |
| n-C$_3$H$_7$ | [Cy-Phe] | F | H |
| n-C$_3$H$_7$ | [Cy-Phe] | F | F C 32 N 111 I; $\Delta n = +0.124$; $\Delta\epsilon = 11.2$ |
| n-C$_5$H$_{11}$ | [Cy-Phe] | F | H |
| n-C$_5$H$_{11}$ | [Cy-Phe] | F | F C 35 N 111 I; $\Delta n = +0.119$; $\Delta\epsilon = 10.7$ |
| H$_2$C=CH— | [Cy-Phe] | F | H |
| H$_2$C=CH— | [Cy-Phe] | F | F |
| C$_2$H$_5$ | [Cy-Cy] | | H |
| C$_2$H$_5$ | [Cy-Cy] | | F |
| n-C$_3$H$_7$ | [Cy-Cy] | | H C 185 S$_B$(179) S$_A$(184) I; $\Delta n = +0.142$; $\Delta\epsilon = 5.3$ |
| n-C$_3$H$_7$ | [Cy-Cy] | | F |
| n-C$_5$H$_{11}$ | [Cy-Cy] | | H C 182 I; $\Delta n = +0.136$; $\Delta\epsilon = 4.3$ |
| n-C$_5$H$_{11}$ | [Cy-Cy] | | F |
| H$_3$C=CH— | [Cy-Cy] | | H |
| H$_3$C=CH— | [Cy-Cy] | | F |
| n-C$_3$H$_7$ | [Phe] | F | H |
| n-C$_3$H$_7$ | [Phe difluoro] | F | F |
| n-C$_5$H$_{11}$ | [Phe trifluoro] | F | H |
| n-C$_5$H$_{11}$ | [Phe trifluoro] | F | F |

Example 2

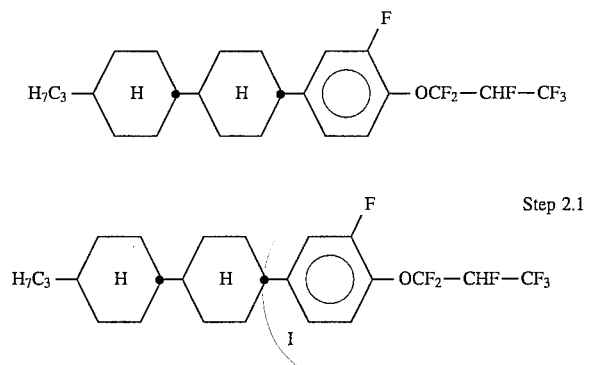

Step 2.1

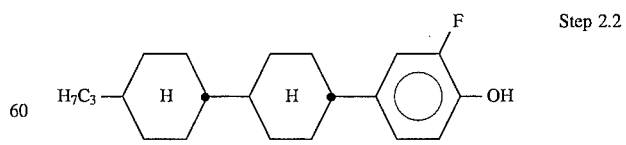

350 mmol of 2-fluorobromobenzene are dissolved in 350 ml of diethyl ether, and the solution is cooled to −70° C. with stirring. 350 mmol of n-BuLi are added dropwise to this solution at −70° C. The mixture is stirred for a further 0.5 hour, and 350 mmol of trans,trans-4-propylcyclohexylcyclohexanone, dissolved in 150 ml of diethyl ether, are added dropwise to the cooled solution. The mixture is allowed to warm to room temperature, hydrolysed and acidified with dilute HCl. The organic phase is separated off, and the aqueous phase is extracted with methyl tert-butyl ether. The combined organic phases are washed with water and dried over Na$_2$SO$_4$. The solvent is removed on a Rotavapor, and the residue is processed further without further purification. 350 mmol of the product are dissolved in 500 ml of toluene, 5 g of p-toluenesulphonic acid are added, and the mixture is boiled for 5 hours on a water separator. The reaction solution is washed until neutral and evaporated. The residue is washed over silica gel and evaporated. 205 mmol of the product are hydrogenated in the presence of Pd-C.

Step 2.2

H$_7$C$_3$—[Cy]—[Cy]—[Phe-F]—OH 0.125 mol of I, 250 ml of THF and 0.137 mol of potassium tert-butoxide are cooled to −100° C. with stirring. 0.1 mol of BuLi (15% in n-hexane) is subsequently added dropwise at from −90° to −100° C. over the course of 40 minutes. The mixture is stirred at −100° C. for 0.5 hour, and 0.143 mol of trimethyl borate is then added dropwise to the solution, and the mixture is stirred for a further 0.5 hour. The temperature of the reaction mixture is allowed to rise to −35° C., HCl and $H_2O_2$ are added and the mixture is subjected to customary work-up.

Step 2.3

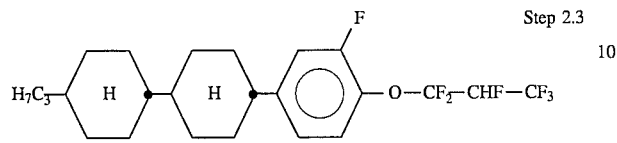

The reaction of the phenol derivative with NaH and hexafluoropropene is carried out analogously to steps 1.1 and 1.2.

The following compounds of the formula

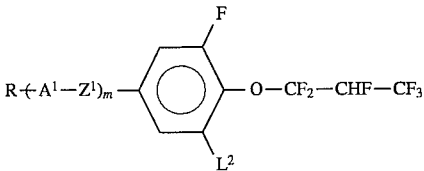

are prepared analagously:

| R | $-(A^1-Z^1)_m-$ | $L^2$ |
|---|---|---|
| $C_2H_5$ | ⬡H—⬡H— | H |
| $C_2H_5$ | ⬡H—⬡H— | F |
| n-$C_3H_7$ | ⬡H—⬡H— | H C 178 I; $\Delta n = +0.0888$; $\Delta \epsilon = 4.7$ |
| n-$C_3H_7$ | ⬡H—⬡H— | F |
| n-$C_5H_{11}$ | ⬡H—⬡H— | H |
| n-$C_5H_{11}$ | ⬡H—⬡H— | F |
| $CH_2=CH-$ | ⬡H—⬡H— | H |
| $CH_2=CH-$ | ⬡H—⬡H— | F |
| $C_2H_5$ | ⬡H—$CH_2CH_2$—⬡H— | H |
| $C_2H_5$ | ⬡H—$CH_2CH_2$—⬡H— | F |
| n-$C_3H_7$ | ⬡H—$CH_2CH_2$—⬡H— | H |

| R | $-(A^1-Z^1)_m-$ | $L^2$ |
|---|---|---|
| n-$C_3H_7$ | cyclohexyl-CH$_2$CH$_2$-cyclohexyl | F |
| n-$C_5H_{11}$ | cyclohexyl-CH$_2$CH$_2$-cyclohexyl | H |
| n-$C_5H_{11}$ | cyclohexyl-CH$_2$CH$_2$-cyclohexyl | F |
| $CH_2=CH-$ | cyclohexyl-CH$_2$CH$_2$-cyclohexyl | H |
| $CH_2=CH-$ | cyclohexyl-CH$_2$CH$_2$-cyclohexyl | F |
| $C_2H_5$ | dioxanyl-cyclohexyl | H |
| $C_2H_5$ | dioxanyl-cyclohexyl | F |
| n-$C_3H_7$ | dioxanyl-cyclohexyl | H |
| n-$C_3H_7$ | dioxanyl-cyclohexyl | F |
| n-$C_5H_{11}$ | dioxanyl-cyclohexyl | H |
| n-$C_5H_{11}$ | dioxanyl-cyclohexyl | F |
| $CH_2=CH-$ | dioxanyl-cyclohexyl | H |
| $CH_2=CH-$ | dioxanyl-cyclohexyl | F |

In the present application and in the examples below, the structures of the liquid-crystal compounds are indicated by acronyms, with the trans formation into chemical formulae being carried out in accordance with Tables A and B below.

All radicals $C_nH_{2n+1}$ and $C_mH_{2m+1}$ are straight-chain alkyl radicals having n or m carbon atoms respectively. The coding in Table B is self-evident. In Table A, only the acronym for the parent structure is shown. In individual cases, the acronym for the parent structure is followed, separated by a dash, by a code for the substituents $R^1$, $R^2$, $L^1$ and $L^2$:

| Code for $R^1$, $R^2$, $L^1$, $L^2$ | $R^1$ | $R^2$ | $L^1$ | $L^2$ |
|---|---|---|---|---|
| nm | $C_nH_{2n+1}$ | $C_mH_{2m+1}$ | H | H |
| nOm | $C_nH_{2n+1}$ | $OC_mH_{2m+1}$ | H | H |
| nO.m | $OC_nH_{2n+1}$ | $C_mH_{2m+1}$ | H | H |
| n | $C_nH_{2n+1}$ | CN | H | H |
| nN.F | $C_nH_{2n+1}$ | CN | H | F |
| nF | $C_nH_{2n+1}$ | F | H | H |
| nOF | $OC_nH_{2n+1}$ | F | H | H |
| nCl | $C_nH_{2n+1}$ | Cl | H | H |
| nF.F | $C_nH_{2n+1}$ | F | H | F |
| nmF | $C_nH_{2n+1}$ | $C_mH_{2m+1}$ | F | H |
| nCF$_3$ | $C_nH_{2n+1}$ | CF$_3$ | H | H |
| nOCF$_3$ | $C_nH_{2n+1}$ | OCF$_3$ | H | H |
| nOCF$_2$ | $C_nH_{2n+1}$ | OCHF$_2$ | H | H |
| nS | $C_nH_{2n+1}$ | NCS | H | H |
| rVsN | $C_rH_{2r+1}-CH=CH-C_sH_{2s}-$ | CN | H | H |
| rEsN | $C_rH_{2r+1}-O-C_2H_{2s}-$ | CN | H | H |
| nNF | $C_nH_{2n+1}$ | CN | F | H |
| nAm | $C_nH_{2n+1}$ | $COOC_mH_{2m+1}$ | H | H |
| nF.Cl | $C_nH_{2n+1}$ | Cl | H | F |

The inventive mixtures especially contain one or more compounds of the formula I and further compounds of the Tables A and B.

TABLE A

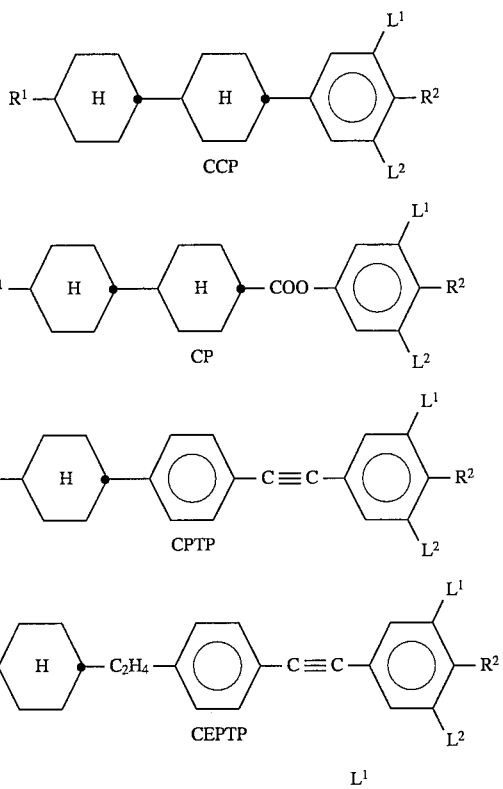

TABLE A-continued

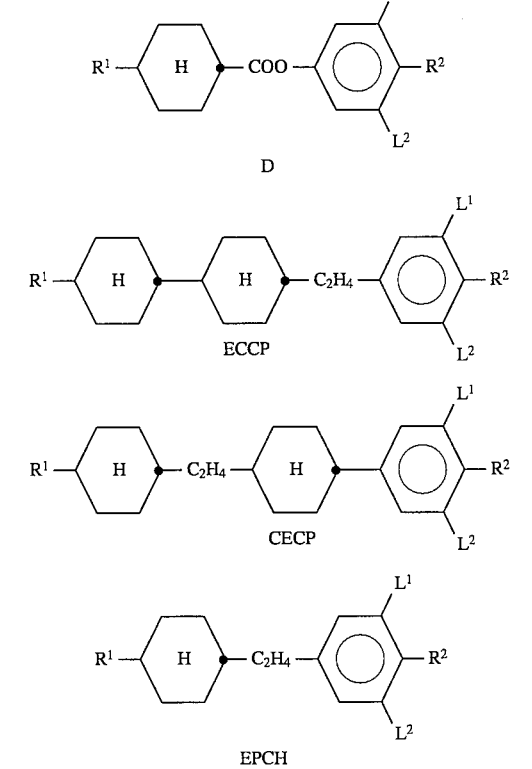

TABLE A-continued
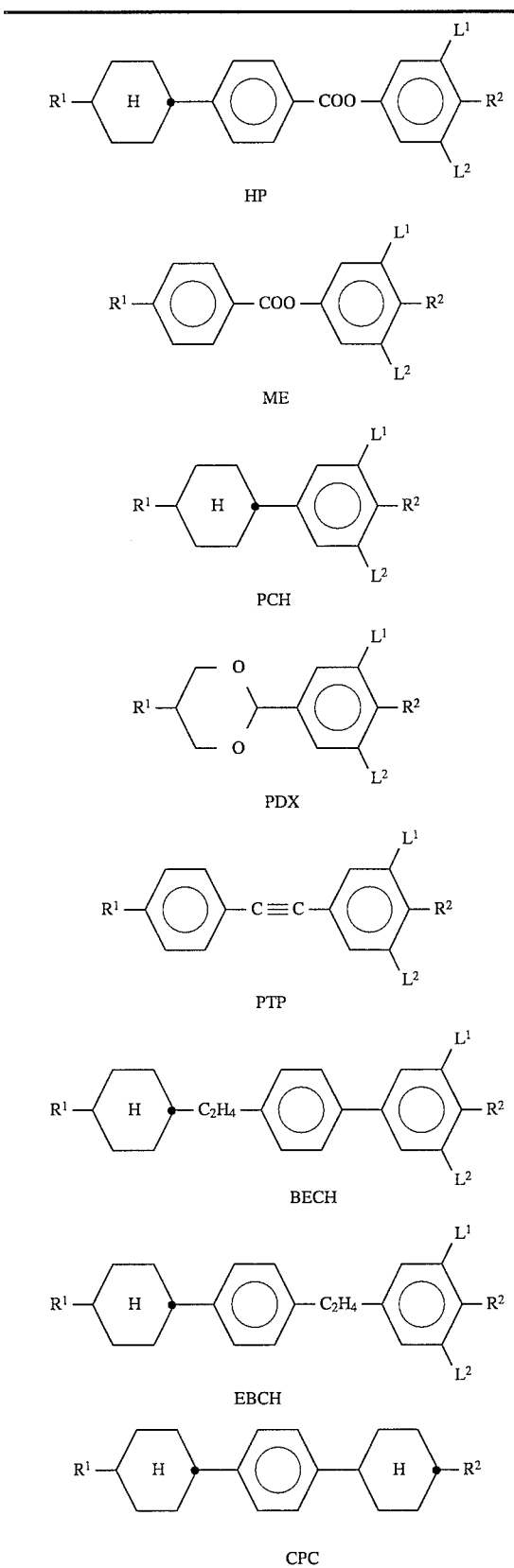
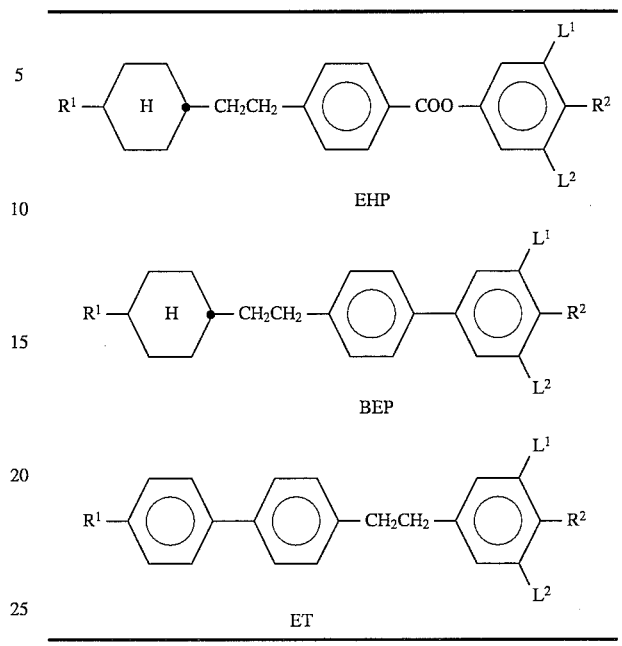
TABLE B
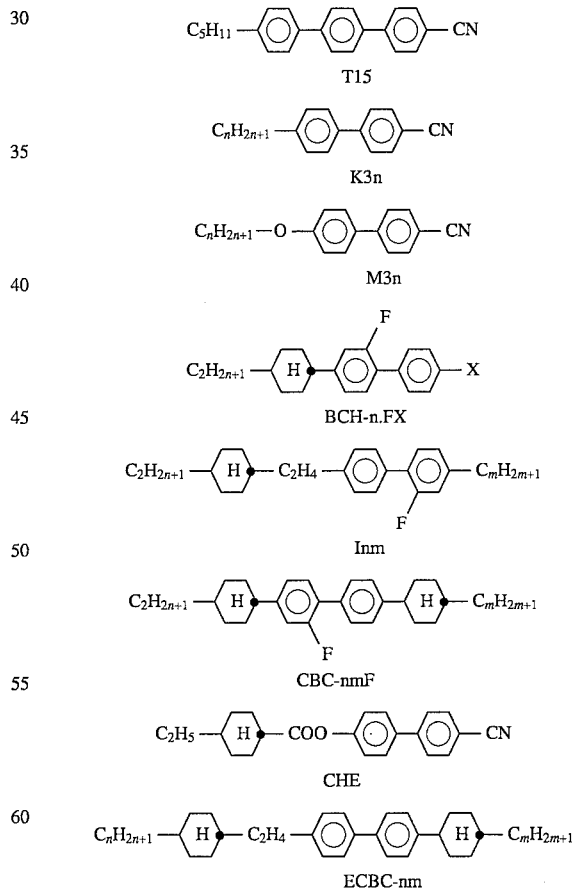

TABLE B-continued $C_nH_{2n+1}$—⟨H⟩—$C_2H_4$—⟨H⟩—$C_mH_{2m+1}$

ECCH-nm $C_nH_{2n+1}$—⟨H⟩—⟨H⟩—$CH_2O$—$C_mH_{2m+1}$

CCH-n1EM $C_nH_{2n+1}$—⟨⟩—⟨F⟩—⟨⟩—CN

T-nFN $C_nH_{2n+1}$—⟨F⟩—⟨⟩—CN

B-nO.FN $C_nH_{2n+1}$—⟨H⟩—⟨⟩—⟨⟩—$OCF_2$—$CHF$—$CF_3$

CPP-n-ODMT $C_nH_{2n+1}$—⟨H⟩—⟨H⟩—⟨⟩—$OCF_2$—$CHF$—$CF_3$

CCP-n-ODMT $C_nH_{2n+1}$—⟨H⟩—⟨F,F⟩—⟨F⟩—$OCF_2$—$CHF$—$CF_3$

CGU-n-ODMT $C_nH_{2n+1}$—⟨H⟩—⟨F,F⟩—⟨F,F⟩—$OCF_2$—$CHF$—$CF_3$

CUU-n-ODMT

Example A

| | | | |
|---|---|---|---|
| PCH-5F | 9,0% | Clearing point [°C.] | 91,7 |
| PCH-6F | 7,2% | Δn [589 nm, 20° C.]: | +0,0993 |
| PCH-7F | 5,4% | Δε [1 kHz, 20° C]: | 5,83 |
| CCP-2OCF₃ | 7,2% | | |
| CCP-3OCF₃ | 10,8% | | |
| CCP-4OCF₃ | 8,1% | | |
| CCP-5OCF₃ | 8,1% | | |
| BCH-3F.F | 10,8% | | |
| BCH-5F.F | 9,0% | | |
| ECCP-3OCF₃ | 4,5% | | |
| ECCP-5OCF₃ | 4,5% | | |
| CBC-33F | 1,8% | | |
| CBC-53F | 1,8% | | |
| CBC-55F | 1,8% | | |
| CGU-3-ODMT | 10,0% | | |

Example B

| | | | |
|---|---|---|---|
| PCH-5F | 9,0% | Clearing point [°C.] | 92,9 |
| PCH-6F | 7,2% | Δn [589 nm, 20° C.]: | +0,0988 |
| PCH-7F | 5,4% | Δε [1 kHz, 20° C.]: | 5,79 |
| CCP-2OCF₃ | 7,2% | | |
| CCP-3OCF₃ | 10,8% | | |
| CCP-4OCF₃ | 8,1% | | |
| CCP-5OCF₃ | 8,1% | | |
| BCH-3F.F | 10,8% | | |
| BCH-5F.F | 9,0% | | |
| ECCP-3OCF₃ | 4,5% | | |
| ECCP-5OCF₃ | 4,5% | | |
| CBC-33F | 1,8% | | |
| CBC-53F | 1,8% | | |
| CBC-55F | 1,8% | | |
| CGU-5-ODMT | 10,0% | | |

Example C

| | | | |
|---|---|---|---|
| PCH-5F | 9,0% | Clearing point [°C.] | 90,7 |
| PCH-6F | 7,2% | Δn [589 nm, 20° C.]: | +0,098 |
| PCH-7F | 5,4% | Δε ]1 kHz, 20° C.]: | 6,07 |
| CCP-2OCF₃ | 7,2% | | |
| CCP-3OCF₃ | 10,8% | | |
| CCP-4OCF₃ | 8,1% | | |
| CCP-5OCF₃ | 8,1% | | |
| BCH-3F.F | 10,8% | | |
| BCH-5F.F | 9,0% | | |
| ECCP-3OCF₃ | 4,5% | | |
| ECCP-5OCF₃ | 4,5% | | |
| CBC-33F | 1,8% | | |
| CBC-53F | 1,8% | | |
| CBC-55F | 1,8% | | |
| CUU-5-ODMT | 10,0% | | |

Example D

| | | | |
|---|---|---|---|
| PCH-5F | 9,0% | Clearing point [°C.] | 89,2 |
| PCH-6F | 7,2% | Δn [589 nm, 20° C.]: | +0,0976 |
| PCH-7F | 5,4% | Δε [1 kHz, 20° C.]: | 6,10 |
| CCP-2OCF₃ | 7,2% | | |
| CCP-3OCF₃ | 10,8% | | |
| CCP-4OCF₃ | 8,1% | | |
| CCP-5OCF₃ | 8,1% | | |
| BCH-3F.F | 10,8% | | |
| BCH-5F.F | 9,0% | | |
| ECCP-3OCF₃ | 4,5% | | |
| ECCP-5OCF₃ | 4,5% | | |
| CBC-33F | 1,8% | | |
| CBC-53F | 1,8% | | |
| CBC-55F | 1,8% | | |
| CUU-3-ODMT | 10,0% | | |

Example E

| | | | |
|---|---|---|---|
| PCH-5F | 9,0% | Clearing point [°C.] | 98.4 |
| PCH-6F | 7,2% | Δn [589 nm, 20° C.]: | 0.1014 |
| PCH-7F | 5,4% | Δε [1 kHz, 20° C.]: | 5.3 |
| CCP-2OCF₃ | 7,2% | ν₂₀ [mm²/s]: | 15.3 |
| CCP-3OCF₃ | 10,8% | | |
| CCP-4OCF₃ | 8,1% | | |
| CCP-5OCF₃ | 8,1% | | |
| BCH-3F.F | 10,8% | | |
| BCH-5F.F | 9,0% | | |
| ECCP-3OCF₃ | 4,5% | | |
| ECCP-5OCF₃ | 4,5% | | |
| CBC-33F | 1,8% | | |
| CBC-53F | 1,8% | | |
| CBC-55F | 1,8% | | |
| CPP-3-ODMT | 10,0% | | |

Example F

| | | | |
|---|---|---|---|
| PCH-5F | 9.0% | Clearing point [°C.]: | 97.2 |
| PCH-6F | 7,2% | Δn [589 nm, 20° C.]: | 0.1005 |
| PCH-7F | 5,4% | Δε [1 kHz, 20° C.]: | 5.2 |
| CCP-2OCF$_3$ | 7,2% | $v_{20}$ [mm$^2$/s]: | 15.4 |
| CCP-3OCF$_3$ | 10,8% | $v_0$ [mm$^2$/s]: | 42 |
| CCP-4OCF$_3$ | 8,1% | | |
| CCP-5OCF$_3$ | 8,1% | | |
| BCH-3F.F | 10,8% | | |
| BCH-5F.F | 9,0% | | |
| ECCP-3OCF$_3$ | 4,5% | | |
| ECCP-5OCF$_3$ | 4,5% | | |
| CBC-33F | 1,8% | | |
| CBC-53F | 1,8% | | |
| CBC-55F | 1,8% | | |
| CPP-5-ODMT | 10,0% | | |

Example G

| | | | |
|---|---|---|---|
| PCH-5F | 9.0% | Clearing Point [°C.]: | 98.7 |
| PCH-6F | 7,2% | Δn [589 nm, 20° C.]: | 0.0960 |
| PCH-7F | 5,4% | Δε [1 kHz, 20° C.]: | 5.2 |
| CCP-2OCF$_3$ | 7,2% | $v_{20}$ [mm$^2$/s]: | 15.2 |
| CCP-3OCF$_3$ | 10,8% | $v_0$ [mm$^2$/s]: | 42.8 |
| CCP-4OCF$_3$ | 8,1% | | |
| CCP-5OCF$_3$ | 8,1% | | |
| BCH-3F.F | 10,8% | | |
| BCH-5F.F | 9,0% | | |
| ECCP-3OCF$_3$ | 4,5% | | |
| ECCP-5OCF$_3$ | 4,5% | | |
| CBC-33F | 1,8% | | |
| CBC-53F | 1,8% | | |
| CBC-55F | 1,8% | | |
| CPP-3-ODMT | 10.0% | | |

Example H

| | | | |
|---|---|---|---|
| PCH-5F | 3,4% | Clearing point [°C.]: | 122 |
| CCP-2OCF$_2$-F.F | 18,1% | Δε [1 kHz, 20° C.]: | 8.8 |
| CCP-3OCF$_2$-F.F | 17,0% | $k_3/k_1$ [20° C.]: | 1.55 |
| CCP-5OCF$_2$-F.F | 18,1% | $k_1$ [10$^{-12}$N] [20° C.]: | 12.1 |
| CUP-2F.F | 5,7% | | |
| CUP-3F.F | 5,7% | | |
| CBC-33F | 5,7% | | |
| CBC-53F | 5,7% | | |
| CBC-55F | 5,6% | | |
| CGU-3-ODMT | 15,0% | | |

Example I

| | | | |
|---|---|---|---|
| PCH-5F | 3,2% | Clearing point [°C.]: | 116 |
| CCP-2OCF$_2$-F.F | 17,0% | Δε [1 kHz, 20° C.]: | 9.8 |
| CCO-3OCF$_2$-F.F | 16,0% | $k_3k_1$ [20° C.]: | 1.59 |
| CCP-5OCF$_2$-F.F | 17,0% | $k_1$ [10$^{-12}$N] [20° C.]: | 11.5 |
| CUP-2F.F | 5,4% | | |
| CUP-3F.F | 5,4% | | |
| CBC-33F | 5,4% | | |
| CBC-53F | 5,4% | | |
| CBC-55F | 5,4% | | |
| CGU-3-ODMT | 20,0% | | |

What is claimed is:

1. A liquid-crystalline medium having at least two liquid-crystalline components wherein at least one of the components is a hexafluoropropyl ether compound of the formula I

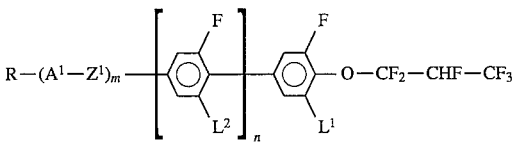

in which

R is H, an alkyl or alkenyl radical having 1 to 15 carbon atoms which is unsubstituted, monosubstituted by CN or CF$_3$ or monosubstituted to perhalo-substituted by halogen, where, optionally, one or more CH$_2$ groups in these radicals are replaced, in each case independently of one another by —O—, —S—,

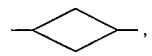

—CO—, —CO—O—, —O—CO— or —O—CO—O in such a way that O and/or S atoms are not bonded directly to one another, A$^1$ is
(a) a trans-1,4-cyclohexylene radical in which one or more non-adjacent CH$_2$ groups can optionally, in each case, be replaced by —O— or —S—,
(b) a 1,4-phenylene radical in which one or two CH groups are optionally replaced by N, or
(c) a 1,4-cyclohexenylene, 1,4-bicyclo[2.2.2]octylene, piperidine-1,4-diyl, naphthalene-2,6-diyl, decahydronaphthalene-2,6-diyl or 1,2,3,4-tetrahydronaphthalene-2,6-diyl, where the radicals (a) and (b) are optionally substituted by one or two fluorine atoms;

Z$^1$ is —CO—O—, —O—CO—, —CH$_2$O—, —OCH$_2$—, —CH$_2$CH$_2$—, —CH=CH—, —C≡C—, —(CH$_2$)$_4$—, —CH=CH—CH$_2$—CH$_2$—, or a single bond;

L$^1$ and L$^2$ are each independently of one another, H or F;

m is 0, 1 or 2;

n is 1; and m+n is ≧1.

2. A liquid-crystalline medium according to claim 1, wherein m=1.

3. A liquid-crystalline medium of claim 1, wherein said hexafluoropropyl ether compound is of the formula I27

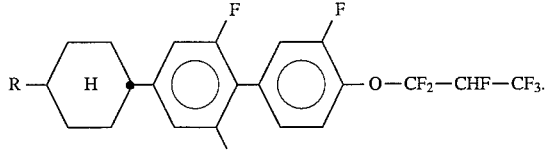

4. A liquid-crystalline medium of claim 1, wherein said hexafluoropropyl ether compound is of the formula I28

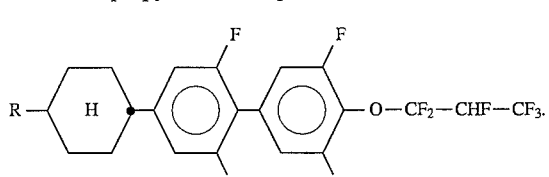

5. A liquid-crystalline medium of claim 1, wherein said hexafluoropropyl ether compound is of the formula I29

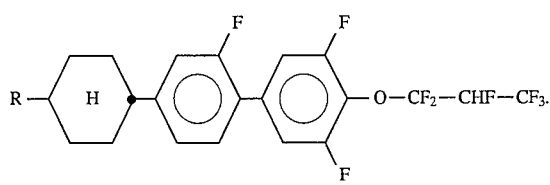

6. A liquid-crystalline medium of claim 1, wherein said hexafluoropropyl ether compound is of the formula I30

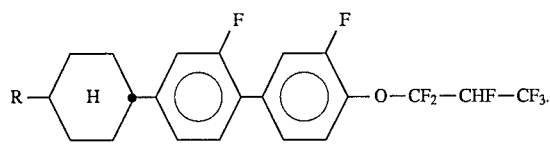

7. In a liquid-crystal display element containing a liquid-crystalline medium, the improvement wherein the liquid-crystalline medium is according to claim 1.

8. The liquid-crystalline medium according to claim 2, wherein $A^1$ is a trans-1,4-cyclohexylene radical and $Z^1$ is a single bond.

9. The liquid crystalline medium of claim 1, comprising 1 to 40% by weight of compounds of the formula I.

10. The liquid crystalline medium of claim 1, comprising 45 to 90% by weight of compounds of the formula I.

11. The liquid crystalline medium of claim 1, comprising 3–5 compounds of the formula I.

* * * * *